(12) United States Patent
Aladahalli et al.

(10) Patent No.: US 10,262,425 B2
(45) Date of Patent: Apr. 16, 2019

(54) SYSTEM AND METHOD FOR LONGITUDINAL DATA PROCESSING (71) Applicant: General Electric Company, Schenectady, NY (US)

(72) Inventors: Chandan Kumar Mallappa Aladahalli, Bangalore (IN); Krishna Seetharam Shriram, Bangalore (IN); Dattesh Dayanand Shanbhag, Bangalore (IN); Sheshadri Thiruvenkadam, Bangalore (IN); Sandeep Suryanarayana Kaushik, Bangalore (IN); Rakesh Mullick, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 96 days.

(21) Appl. No.: 15/637,280

(22) Filed: Jun. 29, 2017

(65) Prior Publication Data
US 2018/0005389 A1    Jan. 4, 2018

(30) Foreign Application Priority Data

Jun. 29, 2016 (IN) .............................. 201641022385

(51) Int. Cl.
*G06F 19/00* (2018.01)
*G06T 7/33* (2017.01)
(Continued)

(52) U.S. Cl.
CPC .............. *G06T 7/33* (2017.01); *A61B 5/0033* (2013.01); *A61B 5/0073* (2013.01); *A61B 5/486* (2013.01);
(Continued)

(58) Field of Classification Search
CPC ..... A61B 5/0073; A61B 5/0515; A61B 5/055; G06F 19/34; G06T 7/0012; G06T 7/11; G06T 7/33
See application file for complete search history.

(56) References Cited

U.S. PATENT DOCUMENTS 8,588,488 B2    11/2013 Bystrov et al.
9,076,201 B1 *   7/2015 Negahdar ............. G06T 7/0012
(Continued)

OTHER PUBLICATIONS

Skup, "Longitudinal fMRI analysis: A review of methods", Statistics and Its Interface, vol. 3, Issue 2, pp. 235-252, 2010.
(Continued)

*Primary Examiner* — Siamak Harandi (57) ABSTRACT

A method for synchronization of a longitudinal data set from a subject includes receiving a first ensemble registration estimate having a first reference image corresponding to a first image ensemble and receiving a second image ensemble different from the first image ensemble. The method includes determining a second reference image based on the second image ensemble and the first reference image. Further, the method includes determining a second ensemble registration estimate based on the first ensemble registration estimate, the second reference image, the first image ensemble and the second image ensemble using an optimization technique. The method further includes generating a synchronized image ensemble corresponding to the first image ensemble and the second image ensemble based on the second ensemble registration estimate. The method also includes determining a medical condition of the subject by a medical practitioner based on the synchronized image ensemble.

19 Claims, 5 Drawing Sheets

(51) Int. Cl.
    *G06T 7/00*         (2017.01)
    *G06T 7/11*         (2017.01)
    *G06Q 50/24*       (2012.01)
    *A61B 5/00*        (2006.01)
    *A61B 5/05*        (2006.01)
    *A61B 5/055*       (2006.01)

(52) U.S. Cl.
    CPC ............... *A61B 5/72* (2013.01); *G06F 19/00* (2013.01); *G06F 19/34* (2013.01); *G06Q 50/24* (2013.01); *G06T 7/0012* (2013.01); *G06T 7/11* (2017.01); *A61B 5/055* (2013.01); *A61B 5/0515* (2013.01)

(56) References Cited

U.S. PATENT DOCUMENTS

| | | |
|---|---|---|
| 2005/0238254 A1 | 10/2005 | Guhring et al. |
| 2006/0225508 A1 | 10/2006 | Sfeir |
| 2007/0086659 A1 | 4/2007 | Chefd et al. |
| 2009/0052756 A1* | 2/2009 | Saddi ................... G06K 9/6209 382/131 |
| 2011/0200227 A1 | 8/2011 | Bogoni et al. |
| 2011/0218405 A1 | 9/2011 | Avinash et al. |
| 2014/0064580 A1 | 3/2014 | Madabhushi et al. |

OTHER PUBLICATIONS

Nioblet et al., "An efficient incremental strategy for constrained groupwise registration based on symmetric pairwise registration", Pattern Recognition Letters, vol. 33, Issue 3, pp. 283-290, 2012.
Muller, "Functional Modeling and Classification of Longitudinal Data", 25 Pages.

* cited by examiner

SYSTEM AND METHOD FOR LONGITUDINAL DATA PROCESSING

CROSS-REFERENCE TO RELATED APPLICATION

This application claims priority to Indian Patent Application No. 201641022385, filed on Jun. 29, 2016, the entirety of which is incorporated herein by reference.

BACKGROUND

Embodiments of the present specification relate generally to image registration, and more particularly to systems and methods for synchronization of time varying longitudinal data sets corresponding to multiple parameters from a plurality of image modalities at a plurality of time instants.

Images of an organ of interest acquired over time by an imaging device are typically similar to one another. However, to establish feature correspondence, it is required to align these images with respect to one another. Synchronization of images may be required when a plurality of imaging modalities acquire images from an organ of interest. In general, image registration techniques are employed in various areas such as remote sensing, recognition, tracking, and diagnostics. In medical field, image registration enables the work of clinicians, radiologists and surgeons in planning and performing surgeries, for example. In applications such as tracking and remote sensing, image registration techniques are used to automatically recognize and tack moving objects.

Image registration techniques typically include identifying a geometric transformation that aligns images into a same coordinate space. One or more geometric transformations used in image registration may be obtained by optimization techniques. In particular, optimization techniques employ a registration model characterized by a plurality of parameters, known as registration parameters. The model determines the type of registration, such as a rigid registration, affine registration, or deformable registration. The registration parameters include, but not limited to, a scaling factor, a linear shift, an angular shift and a transformation function.

In conventional registration techniques, a reference image is used to align a plurality of images. For example, in some of the existing techniques, a pair-wise alignment is achieved and one of the images of the pair is used with a new image for registration. In other techniques, a template based registration is employed. However, these techniques are influenced by selection of the reference image or an average image model.

Group wise registration methods attempt to mitigate uncertainties associated with any one image by simultaneously registering all images in a population. Group-wise registration techniques incorporate information from all images in registration process and eliminate bias towards a chosen reference frame. Synchronization of longitudinal data requires group-wise registration of images in batches. Group-wise registration helps a clinician to analyze a region of interest (ROI) for temporal variations. When a new batch of images is included in the longitudinal data, conventional group-wise registration provides temporal trends inconsistent with the previous results obtained from a subset of longitudinal data. Newer techniques are needed to avoid inconsistencies in interpretation while synchronizing the longitudinal image data.

SUMMARY

In accordance with one aspect of the specification, a method for synchronization of a longitudinal data set from a subject is disclosed. The method includes receiving a first ensemble registration estimate corresponding to a first image ensemble. The first ensemble registration estimate includes a first reference image and a first set of transformations corresponding to a common co-ordinate space. The method also includes receiving a second image ensemble different from the first image ensemble. The first image ensemble and the second image ensemble are part of the longitudinal data set corresponding to the subject. The method also includes determining a second reference image based on the second image ensemble and the first reference image. Further, the method includes determining a second ensemble registration estimate based on the first ensemble registration estimate, the second reference image, the first image ensemble and the second image ensemble using an optimization technique. The second ensemble registration estimate comprises the first set of transformations, a second set of transformations corresponding to the second image ensemble and a reference transformation for transforming the first reference image to the second reference image. The method further includes generating a synchronized image ensemble corresponding to the first image ensemble and the second image ensemble based on the second ensemble registration estimate. The method also includes determining a medical condition of the subject by a medical practitioner based on the synchronized image ensemble.

In accordance with another aspect of the present specification, a system for synchronization of a longitudinal data set from a subject is disclosed. The system includes a database unit configured to store a first ensemble registration estimate corresponding to a first image ensemble. The first ensemble registration estimate includes a first reference image and a first set of transformations corresponding to a common co-ordinate space. The system further includes a data acquisition unit communicatively coupled to an imaging device and the database unit and configured to receive the first ensemble registration estimate from the database unit, the data acquisition unit is further configured to receive a second image ensemble image different from the first image ensemble, from the imaging device. The first image ensemble and the second image ensemble are part of the longitudinal data set corresponding to a subject. The system also includes a processor unit and a memory unit communicatively coupled to the database unit via a communications bus and configured to determine a second reference image based on the first reference image and the second image ensemble. The processor unit is further configured to determine a second ensemble registration estimate corresponding to the second image ensemble based on the first image ensemble, the first ensemble registration estimate, and the second reference image using an optimization technique. The second ensemble registration estimate comprises the first set of transformations, a second set of transformations corresponding to the second image ensemble, the second reference image, and a reference transformation for transforming the first reference image to the second reference image. The processor unit is further configured to generate a synchronized image ensemble based on the first ensemble image ensemble and the second ensemble image ensemble based on the second ensemble registration estimate. The processor unit is also configured to determine a medical condition of the subject by a medical practitioner, based on the synchronized image ensemble.

In accordance with another aspect of the specification, a non-transitory computer readable medium encoded with a program having instructions to instruct at least one processor to synchronize a longitudinal data set from a subject is disclosed. The synchronization technique includes receiving a first ensemble registration estimate corresponding to a first image ensemble. The first ensemble registration estimate includes a first reference image and a first set of transformations corresponding to a common co-ordinate space. The synchronization technique also includes receiving a second image ensemble different from the first image ensemble. The first image ensemble and the second image ensemble are part of the longitudinal data set corresponding to the subject. The synchronization technique also includes determining a second reference image based on the second image ensemble and the first reference image. Further, the synchronization technique includes determining a second ensemble registration estimate based on the first ensemble registration estimate, the second reference image, the first image ensemble and the second image ensemble using an optimization technique. The second ensemble registration estimate comprises the first set of transformations, a second set of transformations corresponding to the second image ensemble and a reference transformation for transforming the first reference image to the second reference image. The synchronization technique further includes generating a synchronized image ensemble corresponding to the first image ensemble and the second image ensemble based on the second ensemble registration estimate. The synchronization technique also includes determining a medical condition of the subject by a medical practitioner based on the synchronized image ensemble.

BRIEF DESCRIPTION OF THE DRAWINGS

These and other features and aspects of embodiments of the present invention will become better understood when the following detailed description is read with reference to the accompanying drawings in which like characters represent like parts throughout the drawings, wherein.

DETAILED DESCRIPTION

As will be described in detail hereinafter, embodiments of systems and methods are related generally to longitudinal data, and more particularly to synchronization of longitudinal data sets corresponding to multiple parameters from a plurality of different image modalities at a plurality of time instants. A first ensemble registration estimate includes a first set of transformations corresponding to a first image ensemble. The first set of transformations is based on a first reference image of the first image ensemble. A subsequent or a second ensemble registration estimate includes a second set of transformations corresponding to a second image ensemble obtained by conducting subsequent examinations. The second set of transformations is based on a second reference image of the first image ensemble and the second image ensemble. A reference transformation for transforming the first reference image to the second reference image is also determined. A synchronized image ensemble is determined based on one or more of the first set of transformations, the second set of transformations, the reference transformation, the first image ensemble, and the second image ensemble.

The terms 'image' and 'image frame' are used herein equivalently and interchangeably and may refer to a 3D image volume or a time varying 3D image data set. The term "longitudinal data set" refers to a plurality of images related to an organ of interest corresponding to a subject, where the plurality of images is acquired over a period of time. The term 'image ensemble' refers to a plurality of images having a time index and in some embodiments may be a subset of the longitudinal data set. The term "transformation" refers to image transformation that includes rotation, translation, deformation and such mathematical operations performed on two dimensional (2D) image volumes, three dimensional (3D), or four dimensional (4D) image volumes. The term 'registration' refers to a process of transforming two or more image frames in an image ensemble to align with a reference image. The term 'co-ordinate space' refers to a vector space having an image ensemble. A basis of the vector space corresponding to the image ensemble may be used for determining a set of transformations for registration. The term 'group-wise registration' refers to a process of transforming a plurality of image frames in an image ensemble to a common co-ordinate space and representing the image ensemble by a reference image. The term "ensemble registration estimate" for a plurality of image frames refers to a reference image and a plurality of transformations corresponding to the plurality of image frames. The term "synchronization" is used to refer to iteratively and/or sequentially registering an unregistered image ensemble with a group-wise registered image ensemble in the common co-ordinate space. The term "reference image" corresponding to a plurality of image frames refers to a registered image corresponding to the plurality of image frames. The term "diagnostic information" refers to an image or in general any information indicative of a medical condition, such as, but not limited to, an abnormality, a progression of an abnormality, reversing of an abnormality to a normal condition, or the like.

Figure 1:
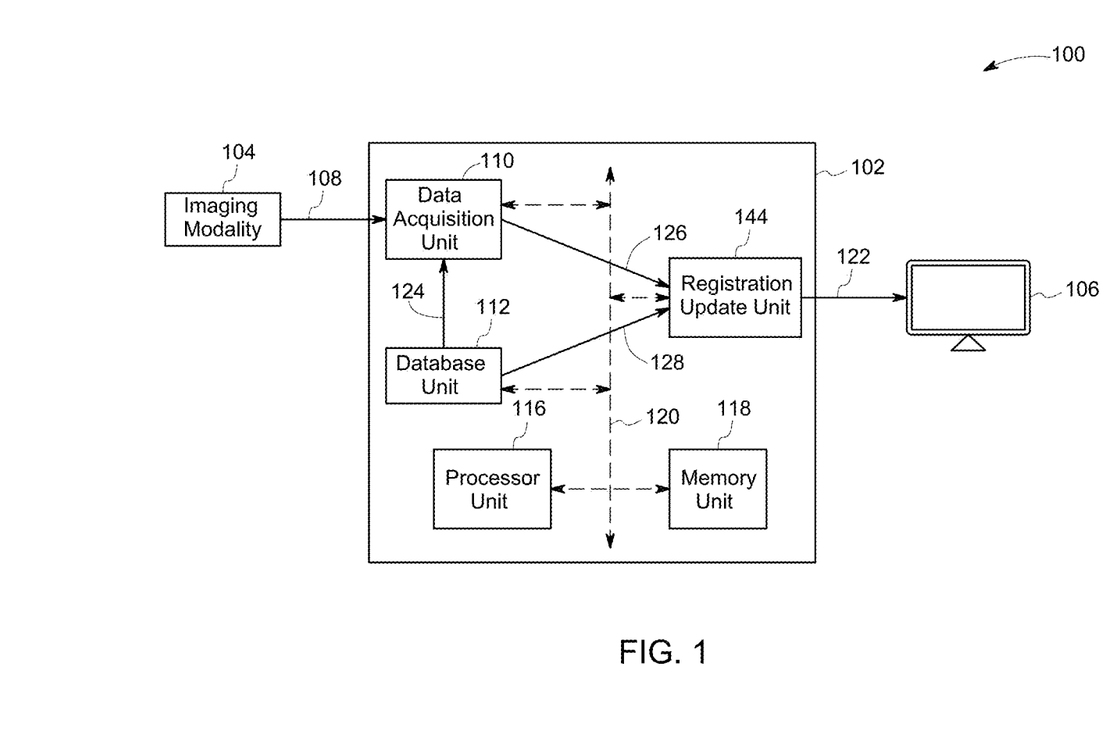
FIG. 1 is a diagrammatic illustration of a system for synchronization of longitudinal data set from a subject, in accordance with an exemplary embodiment.

FIG. 1 is a diagrammatic illustration of a diagnostic system 100 for synchronization of a longitudinal data set 108 from a subject in accordance with an exemplary embodiment. The diagnostic system 100 includes a synchronization unit 102 for performing reference bias free registration of two image ensembles of the longitudinal data set 108. The longitudinal data set 108 may be received from an imaging device 104 or from a memory storing the previously acquisitions. The diagnostic system 100 is configured to generate a synchronized image ensemble 122 and presented to a physician via a display device 106. The synchronization unit 102 includes a data acquisition unit 110, a database unit 112, a registration update unit 114, a processor unit 116, and a memory unit 118 interconnected via a communications bus 120.

The data acquisition unit 110 is communicatively coupled to the imaging device 104 and the database unit 112 and configured to receive the longitudinal data set 108 from the imaging device 104. In one embodiment, the longitudinal data set includes a first image ensemble corresponding to a first time instant and a second image ensemble corresponding to a second time instant. It may be noted that each of the first image ensemble and the second image ensemble includes a plurality of images. The data acquisition unit 110 is configured to receive a first ensemble registration estimate 124 from the database unit 112. In one embodiment, the first ensemble registration estimate 124 includes a first reference image and the first image ensemble is synchronized to the first reference image. The data acquisition unit 110 is further configured to provide a plurality of images 126 to the registration update unit 114. In one embodiment, the plurality of images 126 may include the first image ensemble and the second image ensemble. In another embodiment, the second image ensemble may be acquired in real-time. In some embodiments, the data acquisition unit 110 may be configured to perform pre-processing steps for the plurality of images 126 such as, but not limited to, noise reduction, artifact removal, and data normalization. In one embodiment, the data acquisition unit 110 is further configured to receive a first diagnostic information corresponding to the first ensemble registration estimate, and the first image ensemble from the database unit 112.

The database unit 112 is communicatively coupled to the data acquisition unit 110 and the registration update unit 114 and configured to store the first image ensemble and the first ensemble registration estimate 128. In one embodiment, the first ensemble registration estimate 128 includes a first reference image and a first set of transformations corresponding to the first image ensemble. In one embodiment, the first image ensemble is acquired during a first time period. The database unit 112 may also store a second image ensemble acquired during a second time period, where the second time period occurs after the first time period. The database unit 112 is further configured to provide the first image ensemble 124 to the data acquisition unit 110 and the first ensemble estimate 128 to the registration update unit 114.

The registration update unit 114 is also communicatively coupled to the database unit 112 and configured to receive the first ensemble registration estimate 128. The registration update unit 114 is configured to determine a second ensemble registration estimates based on the second image ensemble. In a first step of determining of the second ensemble estimate, the registration update unit 114 is configured to determine a second reference image corresponding to the second image ensemble. In one embodiment, the second reference image is determined as a weighted mean of images of the second image ensemble and the first reference image. Further, in a second step, the registration update unit 114 is configured to determine the second ensemble estimate based on the first image ensemble, the first ensemble registration estimate, and the second reference image, and the second image ensemble. The second ensemble registration estimate includes a second set of transformations, a second reference image, and a reference transformation along with the first set of transformation and the first reference image. In one embodiment, the registration update unit 114 is configured to determine a plurality of diffeomorphic transformations corresponding to a plurality of transformations of the second ensemble registration estimate. In one embodiment, the registration update unit 114 is further configured to determine a second diagnostic information corresponding to the second ensemble registration estimate and the second image ensemble. The registration update unit 114 is also configured to determine the synchronized image ensemble 122 based on the second ensemble registration estimate, the first image ensemble and the second ensemble. In one embodiment, the synchronized image ensemble further includes the first ensemble registration estimate and the second ensemble registration estimate.

In one embodiment, the registration update unit 114 is configured to determine the second ensemble registration estimate using an optimization technique. Specifically, the registration update unit 114 is configured to minimize an image variance and a deformation field corresponding to an image in the longitudinal data set. The registration update unit 114 is configured to determine a joint cost function to be used in the optimization technique. In one embodiment, the joint cost function is a function of the second set of transformations, and the reference transformation. In another embodiment, the joint cost function also includes a variance based on the first reference image and the second reference image. In one embodiment, the terms of the joint optimization function are representative of energy and the registration update unit 114 is configured to perform minimization of the joint cost function. A second ensemble estimate corresponding to a minimum value of the joint cost function is provided as an optimal estimate by the registration update unit 114. Minimization of the joint cost function may be performed by any of the known optimization techniques such as, but not limited to, a gradient descent technique, a least squares technique, a steepest descent technique, and combinations thereof. The registration update unit 114 determines the second set of transformations, the reference transformation and the second reference image in the common co-ordinate space.

Further, the registration update unit 114 is configured to provide the synchronized image ensemble to a medical practitioner for evaluation of a medical condition of the subject. In one embodiment, the registration update unit 114 is configured to display the synchronized ensemble registration estimate on the display device 106. In other embodiments, the first diagnostic information and the second diagnostic information is determined based on at least one of the first ensemble, the second ensemble, the synchronized image ensemble, the synchronized ensemble registration estimate, the first ensemble registration estimate and the second ensemble registration estimate. In another embodiment, the registration update unit 114 is further configured to display at least one of the first diagnostic information and the second diagnostic information on the display device 106.

The processor unit 116 may include one or more processors. The terms 'processor unit', 'one or more processors' and 'processor' are used equivalently and interchangeably throughout this application. The one or more processors include at least one arithmetic logic unit, a microprocessor, a general purpose controller, or a processor array to perform the desired computations or run the computer program. In certain embodiments, the processor unit 116 may be configured to acquire the longitudinal data set 108. In same or different embodiments, the processor unit 116 may be configured to retrieve the first image ensemble and the first ensemble registration estimate from the database unit 112. Further, the processor unit 116 may be configured to generate second ensemble registration estimate. In one embodiment, the processor unit 116 may be configured to generate the synchronized image ensemble 122 indicative of a health condition of the subject examined by the imaging device 104. The functionality of the processor unit 116 may be limited to one or more of the data acquisition unit 110, the database unit 112, and the registration update unit 114.

While the processor unit 116 is shown as a separate unit, there can be a processor co-located or integrated in one or more of the units 110, 112 and 114. Alternatively, one or more processors can be local or remote, such as a central server or cloud based, and the communications link may be a computer bus, a wired link, or a wireless link or a combination thereof.

The memory unit 118 may be a non-transitory storage medium. For example, the memory unit 118 may be a dynamic random access memory (DRAM) device, a static random access memory (SRAM) device, flash memory or other memory devices. In one embodiment, the memory unit 118 may include a non-volatile memory or similar permanent storage device, media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices. A non-transitory computer readable medium may be encoded with a program having instructions to instruct the one or more processor units to generate a synchronized ensemble registration estimate corresponding to a longitudinal data set. In one embodiment, the instructions enable the one or more processors to perform the functions of the synchronization unit 102 of FIG. 1.

In certain embodiments, one or more of the data acquisition unit 110, the database unit 112, and the registration update unit 114 may be stored in the memory unit 118 and may be executable by the processor unit 116. At least one of the units 110, 112, 114 may be standalone hardware components. Other hardware implementations such as field programmable gate arrays (FPGA), application specific integrated circuits (ASIC) or customized chip may be employed for one or more of the units of the synchronization unit 102.

Figure 2:
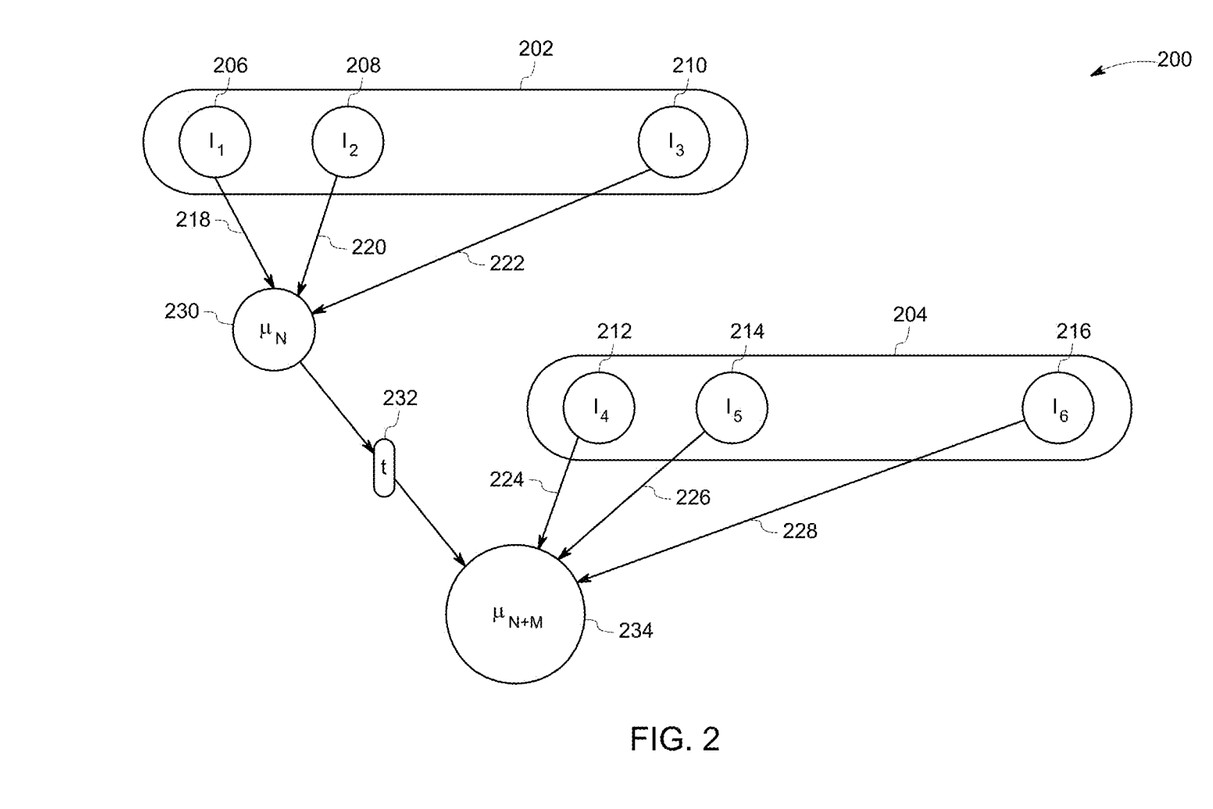
FIG. 2 is a schematic representation of ensemble registration estimates corresponding to two time instants in accordance with an exemplary embodiment.

FIG. 2 is a schematic 200 representation of ensemble registration estimates corresponding to two time instants in accordance with an exemplary embodiment. The schematic 200 includes a first image ensemble 202 having three image frames 206, 208, 210 acquired up to a first time instant. The first ensemble registration estimate corresponding to the first image ensemble 202 includes a first set of transformations having three transformations 218, 220, 222 and a first reference image 230. In general, the first image ensemble may include N image frames. The first ensemble registration estimate corresponding to the first image ensemble is determined by minimizing a first cost function having image-wise variance across all pixels. The first cost function, representative of conventional ensemble cost function, is given by equation (1) represented by:

$$E[t_1, t_2, \ldots, t_N, \mu_N] = \sum_{k=1}^{N} \int_\Omega (I_k(t_k) - \mu_N)^2 dx + \lambda \sum_{k=1}^{N} S(t_k) \quad \text{equation (1)}$$

where, $\mu_N$ is a first reference image, $t_1, t_2, \ldots, t_N$ are a plurality of transformations in the first set of transformations, $I_k(t_k)$ is a transformed image obtained by transformation of image frame $I_k$ by a transformation $t_k$. The term $\lambda$ is a weighting parameter and $S(t_k)$ is a smooth deformation field corresponding to the transformation $t_k$. In one embodiment, the cost function of equation (1) is minimized iteratively to determine the plurality of transformations and the first reference image. In one embodiment, the first reference image is determined in each iteration as represented by equation (2):

$$\mu_N = \frac{1}{N} \sum_{k=1}^{N} I_k(t_k) \quad \text{equation (2)}$$

where, $\mu_N$ is the mean image. In alternate embodiments, the reference image is a group registered image in the common co-ordinate space.

The schematic 200 further includes a second image ensemble 204 having another three image frames 212, 214, 216 acquired after the first time instant and up to a second time instant. The second ensemble registration estimate corresponding to the second image ensemble 204 includes a second set of transformations having three transformations 224, 226, 228, and a second reference image 234. In one embodiment, the second reference image is representative of a reference image corresponding to union of the first image ensemble and the second image ensemble. The second reference image is determined based on the first reference image and the second image ensemble. The second ensemble registration estimate also includes a reference transformation 232 that transforms the first reference image 230 to the second reference image 234. In general, the second image ensemble includes M image frames. Embodiments of the present technique determine the second image ensemble and the reference transformation based on the first ensemble estimate and the second image ensemble.

In one embodiment, the second ensemble estimate is determined by minimizing a second cost function representative of updated variance across pixels of N+M image frames. The second cost function is given by equation (3):

$$E[t, t_{N+1}, t_{N+2}, \ldots, t_{N+M}, \mu_{N+M}] = \quad \text{equation (3)}$$

$$\sum_{k=1}^{N} \int_\Omega (I_k(t_k \cdot t) - \mu_{N+M})^2 dx +$$

$$\sum_{k=N+1}^{N+M} \int_\Omega (I_k(t_k) - \mu_{N+M})^2 dx + \lambda \sum_{k=N+1}^{N+M} S(t_k) + \lambda_t S[t]$$

where, t is a reference transformation for registering the first reference image 230, to the second reference image 234, $t_{N+1}, t_{N+2}, \ldots, t_{N+M}$ are a plurality of transformations in the second set of transformations and $\mu_{N+M}$ is the second reference image 234. The reference transformation t is a diffeomorphic transformation ensuring consistency of the first ensemble registration estimate and the second ensemble registration estimate. The first term in the right hand side of equation (3) having N summation terms, is representative of contribution of the first image ensemble to the variance with the second reference image, the second term is representative of contribution of the second image ensemble to the variance, and the last two terms each having M+N summation terms, are representative of smooth deformation fields corresponding to the second image ensemble and the first image ensemble, respectively.

In another embodiment, the second ensemble estimate is determined by minimizing a third cost function representative of updated variance across pixels of the N+M image frames. The third cost function is given by equation (4):

$$E[t, t_{N+1}, t_{N+2}, \ldots, t_{N+M}, \mu_{N+M}] = \quad \text{equation (4)}$$

$$N \int_\Omega (\mu_N(t) - \mu_{N+M})^2 dx +$$

$$\sum_{k=N+1}^{N+M} \int_\Omega (I_k(t_k) - \mu_{N+M})^2 dx + \lambda \sum_{k=N+1}^{N+M} S(t_k) + \lambda_1 S[t]$$

where, $\mu_N$ is first reference image, $\mu_{N+M}$ is the second reference image and the first term in the right hand side of the equation (4) is representative of variance between the first reference image and the second reference image. The second reference image $\mu_{N+M}$ is represented as:

$$(N+M)\mu_{N+M} = N\mu_N + \sum_{k=N+1}^{N+M} I_k(t_k) \quad \text{equation (5)}$$

Euler-Lagrange equation for the reference transformation t corresponding to the equation (3) is given by:

$$\sum_{k=1}^{N} (I_k(t_k \cdot t) - \mu_{N+M}) \partial I_k(t_k \cdot t) + \lambda_t S[t] = 0 \quad \text{equation (6)}$$

and the Euler-Lagrange equation for the reference transformation t corresponding to the equation (4) is given by:

$$\sum_{k=1}^{N} (\mu_N(t) - \mu_{N+M}) \partial \mu_N(t) + \lambda_t S[t] = 0 \quad \text{equation (7)}$$

where, δ is representative of gradient function and the Euler-Lagrange equation is used in gradient based optimization techniques.

Figure 3A:
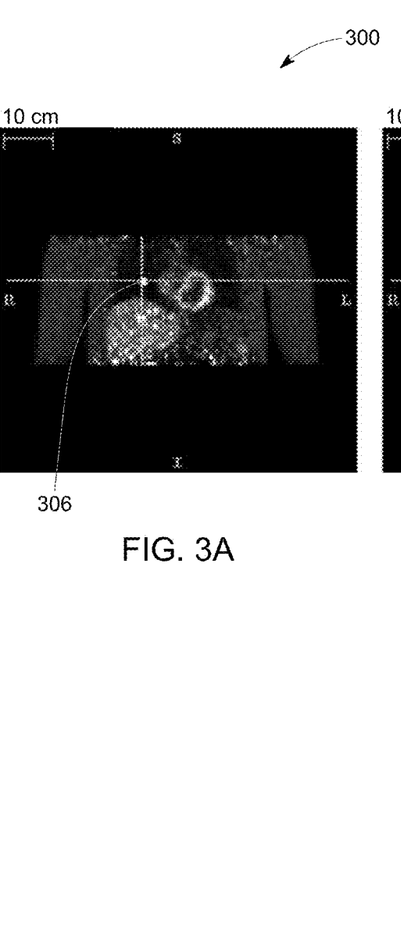
FIGS. 3A-3C are images corresponding to a plurality of time instants synchronized by an ensemble registration technique, in accordance with an exemplary embodiment.
Figure 3B:
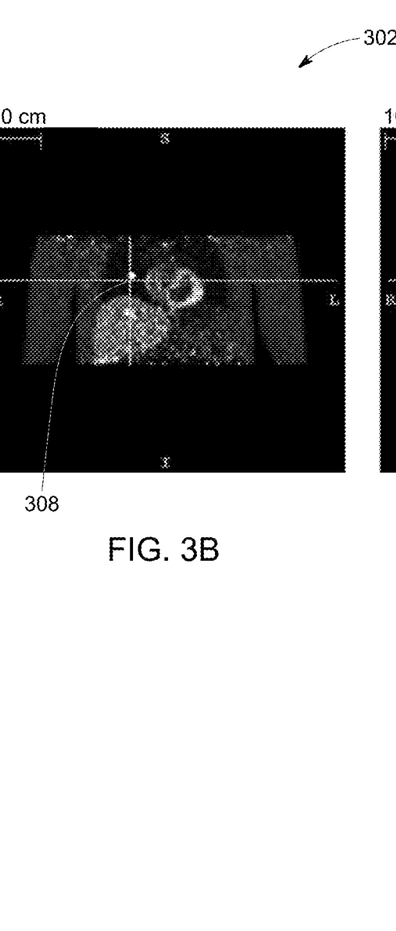
Figure 3C:
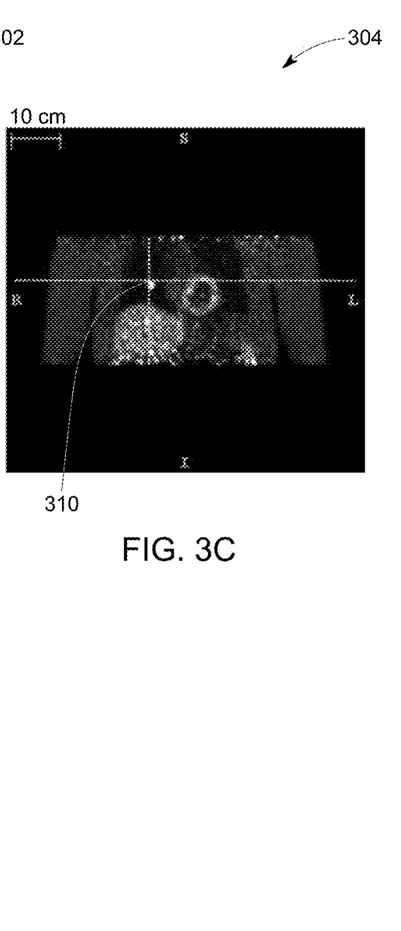

FIGS. 3A-3C illustrate a plurality of image frames of a longitudinal data set to be registered by an ensemble registration technique in accordance with an exemplary embodiment. FIG. 3A is a first image 300 of the first image ensemble and FIG. 3B is a second image 302 of the first image ensemble of the longitudinal data set. FIG. 3C is a third image 304 of the second image ensemble of the longitudinal data set. The first image 300 includes a point 306 representative of a lesion location. The second image 302 includes a point 308 representative of lesion location corresponding to the point 306 of FIG. 3A. The third image 304 includes a point 310 representative of a lesion location corresponding to the point 306 of FIG. 3A. As can be noted, the lesion locations 306, 308, 310 are not exactly same in the plurality of images 300, 302, 304. A first ensemble estimate corresponding to the first image 300 and the second image 302 is used for registering the first image 300 with the second image 302. A second ensemble estimate corresponding to the second image ensemble having the third image 304 is determined by the disclosed technique based on the first image ensemble and the first ensemble estimates. The first ensemble estimates and the second ensemble estimate is used to generate a synchronized ensemble registration estimate of the longitudinal data set having the plurality of image frames 300, 302, 304. The synchronized ensemble registration estimate may be used to register the first image 300, the second image 302 with the third image 304.

Figure 4A:
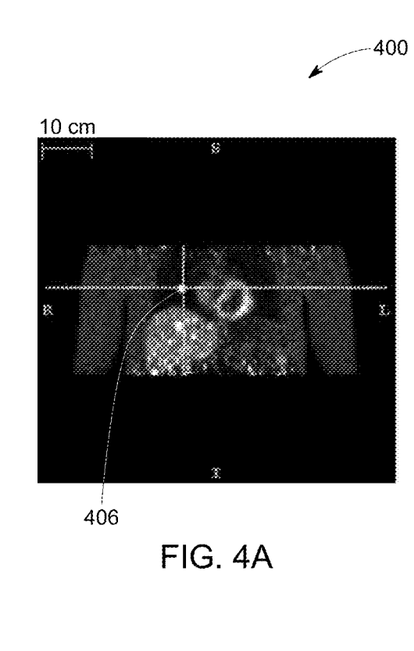
FIGS. 4A-4C are images corresponding to a plurality of time instants synchronized by an ensemble registration technique in accordance with an exemplary embodiment.
Figure 4B:
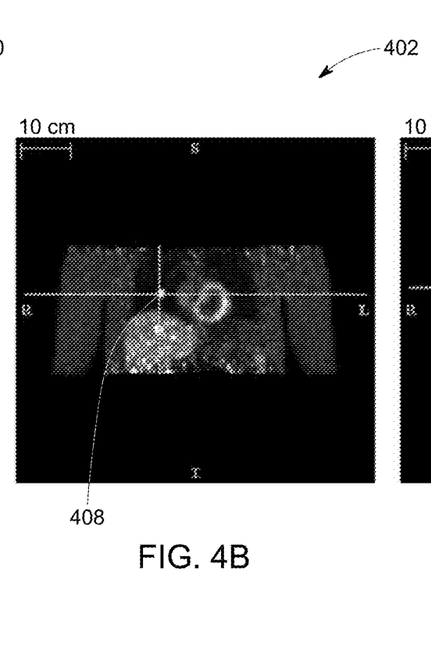
Figure 4C:
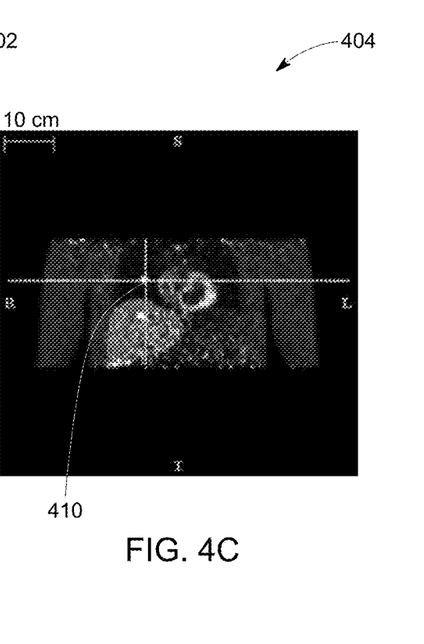

FIGS. 4A-4C illustrate images corresponding to a plurality of registered image frames using an ensemble registration technique in accordance with an exemplary embodiment. FIG. 4A illustrates a first image frame 400, FIG. 4B illustrates a second image frame 402, and FIG. 4C illustrates a third image frame 404 corresponding to the first image 300 of FIG. 3A, the second image frame 302 of FIG. 3B, and the third image frame 304 of FIG. 3C respectively. The image 400 is a registered image obtained by transforming the first image frame 300 using a corresponding transformation (a first transform) from the first set of transformations. The image 402 is a registered image obtained by transforming the second image 302 using a second transformation and the reference transformation. The second transformation transforms the second image 302 to the first reference image and the reference transformation transforms the first reference image to the second reference image. Further, the third image 404 is registered image obtained by transforming the first image 300 using the first transformation, reference transformation and the second set of transformations. Initially, the first image 300 may be transferred to the second reference image using the first reference image and the reference transformation. Subsequently, the second reference image is transformed into the third image 404 using a corresponding inverse transformation from the second set of transformations. The first image 400 includes a point 406 representative of lesion location corresponding to the point 306 of FIG. 3A. The second image 402 includes a point 408 representative of lesion location corresponding to the point 308 of FIG. 3B. The third image 404 includes a point 410 representative of lesion location corresponding to the point 308 of FIG. 3C.

Figure 5:
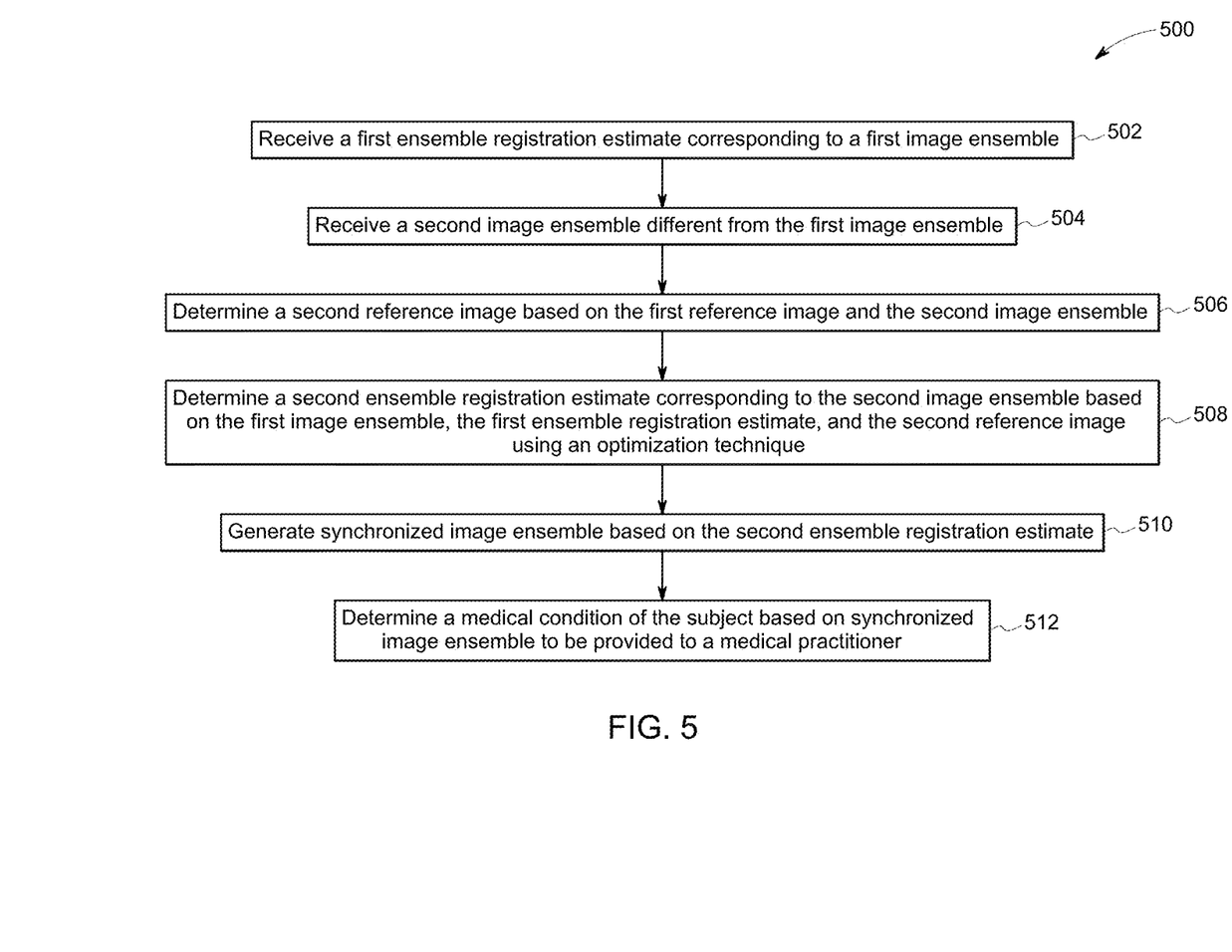
FIG. 5 is a flow chart illustrating a method for synchronization of longitudinal data set from a subject in accordance with an exemplary embodiment.

FIG. 5 is a flow chart 500 illustrating a method for synchronization of longitudinal data sets in accordance with an exemplary embodiment. The method includes receiving a first ensemble registration estimate corresponding to a first image ensemble as indicated in step 502. The first ensemble registration estimate includes a first reference image and a first set of transformations corresponding to the first image ensemble. The first image ensemble includes a plurality of images synchronized in a common coordinate space and represented by the first reference image. Each transformation in the first set of transformations is configured to transform a corresponding image in the first image ensemble to the first reference image. The method also includes receiving a second image ensemble different from the first image ensemble in step 504. The first image ensemble and the second image ensemble are part of a longitudinal data set acquired from an imaging device corresponding to a subject. The second image ensemble includes a plurality of images that are not registered in a group-wise manner and are not synchronized with the first image ensemble.

The method further includes determining a second reference image based on the first reference image and the second image ensemble in step 506. The step of determining the second reference image includes determining a weighted reference of a plurality of images of the second image ensemble and the first reference image. The method includes determining a second ensemble registration estimate corresponding to the second image ensemble based on the first image ensemble, the first ensemble registration estimate, and the second reference image using an optimization technique as indicated in step 508. In one embodiment, the step of determining the second ensemble registration estimate includes minimizing a joint cost function of the second set of transformations and the reference transformation. The joint cost function includes an image variance and a deformation field corresponding to an image in the longitudinal data set. In one example, the optimization technique is based on a steepest descent technique. The optimization technique ensures that the first ensemble registration estimate is not changed while determining the second ensemble registration estimate.

The second ensemble registration estimate includes a second reference image, a second set of transformations corresponding to the second image ensemble and a reference transformation for transforming the first reference image to the second reference image. The reference transformation and each of the second set of transformations are diffeomorphic transformations. The second set of transformations synchronizes the second image ensemble to the common co-ordinate space determined by the first set of transformations and the first reference image. In one embodiment, a synchronized ensemble estimate is determined based on the first ensemble estimate and the second ensemble estimate. The method also includes generating a synchronized image ensemble based on the first ensemble registration estimate, the second ensemble registration estimate, the first image ensemble, and the second image ensemble 510.

In one embodiment, the step of 512 includes determining a medical condition of the subject based on at least one of the synchronized ensemble registration estimate and the synchronized image ensemble. In one embodiment, the medical condition may be determined by a medical practitioner receiving the synchronized ensemble registration estimate. In another embodiment the medical condition may be determined automatically based on the synchronized image ensemble. In some embodiments, the first ensemble estimate may be used to generate first diagnostic information and the second ensemble estimate may be used to generate the second diagnostic information. Further, the medical condition may be determined based on the first diagnostic information and the second diagnostic information. In another embodiment, the step 512 includes receiving first diagnostic information corresponding to the first ensemble registration estimate, and the first image ensemble and generating second diagnostic information based on the second ensemble registration estimate, and the second image ensemble.

In one embodiment, providing the synchronized ensemble registration estimate includes displaying an image from the first image ensemble and an image from a synchronized image ensemble corresponding to the second ensemble simultaneously on a display device. In another embodiment, a subset of images from the synchronized image ensemble may be provided to the medical practitioner for identifying a medical condition of the subject. In an alternate embodiment, at least one of the parameters of the first ensemble registration estimate and the second ensemble registration estimate may be used to determine a medical condition of the subject.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

We claim:

1. A method for synchronization of a longitudinal data set from a subject, comprising:
    receiving a first ensemble registration estimate corresponding to a first image ensemble, wherein the first ensemble registration estimate comprises a first reference image and a first set of transformations corresponding to a common co-ordinate space;
    receiving a second image ensemble different from the first image ensemble, wherein the first image ensemble and the second image ensemble are part of the longitudinal data set corresponding to the subject;
    determining a second reference image based on the second image ensemble and the first reference image;
    determining a second ensemble registration estimate based on the first ensemble registration estimate, the second reference image, the first image ensemble and the second image ensemble using an optimization technique, wherein the second ensemble registration estimate comprises the first set of transformations, a second set of transformations corresponding to the second image ensemble and a reference transformation for transforming the first reference image to the second reference image;
    generating a synchronized image ensemble corresponding to the first image ensemble and the second image ensemble based on the second ensemble registration estimate; and
    determining a medical condition of the subject by a medical practitioner based on the synchronized image ensemble.

2. The method of claim 1, wherein the synchronized image ensemble comprises the first image ensemble and the second image ensemble synchronized with the first image ensemble in the common co-ordinate space.

3. The method of claim 2, wherein determining the medical condition comprises displaying an image from the first image ensemble and an image from a synchronized image ensemble corresponding to the second ensemble simultaneously on a display device.

4. The method of claim 1, wherein determining the second reference image comprises determining a weighted reference of the second image ensemble and the first image ensemble.

5. The method of claim 1, wherein the reference transformation and each of the second set of transformations are diffeomorphic transformations.

6. The method of claim 1, wherein determining the second ensemble registration estimate comprises minimizing a joint cost function of the second set of transformations, and the reference transformation.

7. The method of claim 6, wherein the joint cost function is based on an image ensemble variance and a deformation field corresponding to an image in the longitudinal data set.

8. The method of claim 7, wherein the image variance is based on the first reference image, the second reference image and the reference transformation.

9. The method of claim 1, wherein the optimization technique is based on a steepest descent technique.

10. A system for synchronization of a longitudinal data set from a subject, comprising:
a database unit configured to store a first ensemble registration estimate corresponding to a first image ensemble, wherein the first ensemble registration estimate comprises a first reference image and a first set of transformations corresponding to a common co-ordinate space;
a data acquisition unit communicatively coupled to an imaging device and the database unit and configured to:
receive the first ensemble registration estimate from the database unit; and
receive a second image ensemble image different from the first image ensemble, from the imaging device, wherein the first image ensemble and the second image ensemble are part of the longitudinal data set corresponding to a subject;
a processor unit and a memory unit communicatively coupled to the database unit via a communications bus and configured to:
determine a second reference image based on the first reference image and the second image ensemble;
determine a second ensemble registration estimate corresponding to the second image ensemble based on the first image ensemble, the first ensemble registration estimate, and the second reference image using an optimization technique, wherein the second ensemble registration estimate comprises the first set of transformations, a second set of transformations corresponding to the second image ensemble, the second reference image, and a reference transformation for transforming the first reference image to the second reference image;
generate a synchronized image ensemble based on the first ensemble image ensemble and the second ensemble image ensemble based on the second ensemble registration estimate; and
determine a medical condition of the subject by a medical practitioner, based on the synchronized image ensemble.

11. The system of claim 10, wherein the processor unit is further configured to synchronize the second image ensemble with the first image ensemble in the common co-ordinate space.

12. The system of claim 11, wherein the processor unit is further configured to display displaying an image from the first image ensemble and an image from a synchronized image ensemble corresponding to the second ensemble simultaneously on a display device.

13. The system of claim 10, wherein the processor unit is further configured to determine a weighted reference of the second image ensemble and the first reference image.

14. The system of claim 10, wherein the processor unit is further configured to determine a diffeomorphic transformation corresponding to each of the second set of transformations and the reference transformation.

15. The system of claim 10, wherein the processor unit is further configured to minimize a joint cost function based on the second set of transformations, and the reference transformation to determine the second ensemble registration estimate.

16. The system of claim 15, wherein the processor unit further configured to minimize an image variance and a deformation field corresponding to an image in the longitudinal data set.

17. The system of claim 16, wherein the processor unit is further configured to determine the image variance based on the first reference image, the second reference image and the reference transformation.

18. The system of claim 10, wherein the processor unit is further configured to use a steepest descent technique.

19. A non-transitory computer readable medium encoded with a program having instructions to instruct at least one processor unit to synchronize a longitudinal data set from a subject, the synchronization technique comprising:
receiving a first ensemble registration estimate corresponding to a first image ensemble, wherein the first ensemble registration estimate comprises a first reference image and a first set of transformations corresponding to a common co-ordinate space;
receiving a second image ensemble different from the first image ensemble, wherein the first image ensemble and the second image ensemble are part of the longitudinal data set corresponding to the subject;
determining a second reference image based on the second image ensemble and the first reference image;
determining a second ensemble registration estimate based on the first ensemble registration estimate, the second reference image, the first image ensemble and the second image ensemble using an optimization technique, wherein the second ensemble registration estimate comprises the first set of transformations, a second set of transformations corresponding to the second image ensemble and a reference transformation for transforming the first reference image to the second reference image;
generating a synchronized image ensemble corresponding to the first image ensemble and the second image ensemble based on the second ensemble registration estimate; and
determining a medical condition of the subject by a medical practitioner based on the synchronized image ensemble.

* * * * *